United States Patent
Peglion et al.

(10) Patent No.: US 6,420,413 B2
(45) Date of Patent: Jul. 16, 2002

(54) HETEROCYCLOALKYLBENZO-CYCLOBUTANE AND HETEROARYLBENZOCYCLOBUTANE COMPOUNDS

(75) Inventors: Jean-Louis Peglion, Le Vesinet; Aimée Dessinges, Rueil Malmaison; Bertrand Goument, Viroflay; Mark Millan, Le Pecq; Françoise Lejeune, Saint Cloud; Mauricette Brocco, Paris, all of (FR)

(73) Assignee: Les Laboratories Servier, Neuilly-sur-Seine (FR)

( * ) Notice: Subject to any disclaimer, the term of this patent is extended or adjusted under 35 U.S.C. 154(b) by 0 days.

(21) Appl. No.: 09/833,827

(22) Filed: Apr. 12, 2001

(30) Foreign Application Priority Data

Apr. 13, 2000 (FR) .............................. 00 04742

(51) Int. Cl.$^7$ .................... C07D 209/70; A01K 31/403

(52) U.S. Cl. .................. 514/411; 514/443; 514/468; 514/656; 548/427; 549/43; 549/458; 564/427

(58) Field of Search .................. 548/427; 549/43, 549/458; 564/427; 514/411, 443, 468, 656

(56) References Cited

FOREIGN PATENT DOCUMENTS

WO    WO 9529177    * 11/1995 ................ 548/427

* cited by examiner

*Primary Examiner*—Robert Gerstl
(74) *Attorney, Agent, or Firm*—The Firm of Hueschen and Sage; G. Patrick Sage

(57) ABSTRACT

A compound selected from those of formula (I):

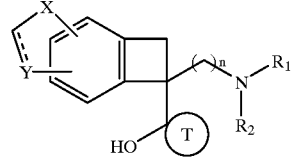

(I)

wherein:

─── denotes single bond or double bond, n is integer from 1 to 6 inclusive, $R_1$, and $R_2$ represent a group selected from hydrogen, linear or branched ($C_1$–$C_6$)-alkyl, aryl, arylalkyl, cycloalkyl, cycloalkylalkyl, alkenyl, alkynyl, heterocycloalkyl, heterocycloalkylalkyl, heteroaryl, and heteroarylalkyl, X represents a group selected from —CH=CH—, oxygen, $S(O)_m$ wherein m is integer from 0 to 2 inclusive, and $NR_3$ wherein $R_3$ represents a group as defined in the description, Y represents CH or $CH_2$ depending on whether ─── denotes single bond or double bond, or may have the additional meaning of oxygen when X represents oxygen, T represents monocyclic or polycyclic ($C_3$–$C_{10}$) cycloalkyl optionally containing within the ring system oxygen, selenium, $S(O)_p$, $NR_3$, or $SiR_4R_5$ wherein p, $R_3$, $R_4$, and $R_5$ are as defined in the description, its isomers and addition salts thereof with a pharmaceutically-acceptable acid or base, and medicinal products containing the same are useful in the treatment of CNS disorders.

15 Claims, No Drawings

HETEROCYCLOALKYLBENZOCYCLOBUTANE AND HETEROARYLBENZOCYCLOBUTANE COMPOUNDS

FIELD OF THE INVENTION

The present invention relates to new heterocycloalkylbenzocyclobutane and heteroarylbenzocyclobutane compounds, and to pharmaceutical compositions containing them.

The compounds of the present invention act as powerful serotonin and noradrenalin reuptake inhibitors. As such, they are useful as medicaments in the treatment of depression, panic attacks, obsessive-compulsive disorders, phobias, impulsive disorders, drug abuse, anxiety, obesity and bulimia.

Indeed, the compounds of the present invention have shown themselves to be active, on the one hand, in vitro in the characterisation test for the inhibition of serotonin and noradrenalin reuptake and, on the other hand, in vivo. Accordingly, in the microdialysis experiments carried out in rat frontal cortex, the compounds of the invention bring about, in that area, an increase in the release of serotonin, noradrenalin and dopamine. The compounds claimed by the Applicant are therefore entirely suited to use in pathologies which are associated with a defect in the transmission of those two neuromediators. That especially valuable effect of the compounds of the invention is also demonstrated in the marble-burying test in mice.

DETAILED DESCRIPTION OF THE INVENTION

More especially, the present invention relates to compounds of formula (I):

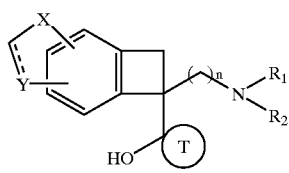

wherein:

----- denotes a single bond or a double bond, n is an integer from 1 to 6 inclusive, $R_1$ and $R_2$, which may be identical or different, each independently of the other represent a group selected from a hydrogen atom, a linear or branched ($C_1$–$C_6$) alkyl group, an aryl group, an aryl-($C_1$–$C_6$)alkyl group in which the alkyl moiety is linear or branched, a cycloalkyl group, a cycloalkyl-($C_1$–$C_6$)alkyl group in which the alkyl moiety is linear or branched, a linear or branched ($C_2$–$C_6$)alkenyl group, a linear or branched ($C_2$–$C_6$)alkynyl group, a heterocycloalkyl group, a heterocycloalkyl-($C_1$–$C_6$)alkyl group in which the alkyl moiety is linear or branched, a heteroaryl group, and a heteroaryl-($C_1$–$C_6$)alkyl group in which the alkyl moiety is linear or branched, X represents a group selected from —CH=CH—, an oxygen atom, a group $S(O)_m$ wherein m is an integer from 0 to 2 inclusive, and $NR_3$ wherein $R_3$ represents a group selected from a hydrogen atom, a linear or branched ($C_1$–$C_6$)alkyl group, an aryl group, an aryl-($C_1$–$C_6$)alkyl group in which the alkyl moiety is linear or branched, a cycloalkyl group, a cycloalkyl-($C_1$–$C_6$) alkyl group in which the alkyl moiety is linear or branched, a linear or branched ($C_2$–$C_6$)alkenyl group, and a linear or branched ($C_2$–$C_6$)alkynyl group, Y represents a CH or $CH_2$ group depending on whether ----- denotes a single bond or a double bond, or may have the additional meaning of an oxygen atom when X represents an oxygen atom, T represents a monocyclic or polycyclic ($C_3$–$C_{12}$) cycloalkyl group, wherein one of the carbon atoms of the cycloalkyl may optionally be replaced by a group selected from an oxygen atom, a selenium atom, a group of formula $S(O)_p$ wherein p is an integer from 0 to 2 inclusive, $NR_3$ wherein $R_3$ is as defined hereinbefore, and $SiR_4R_5$ wherein $R_4$ and $R_5$, which may be identical or different, represent a linear or branched ($C_1$–$C_6$)alkyl group, their isomers and addition salts thereof with a pharmaceutically acceptable acid or base.

"Aryl group" is understood to mean a group selected from phenyl, biphenyl, naphthyl, dihydronaphthyl, tetrahydronaphthyl, indanyl, indenyl and benzocyclobutyl, it being possible for each of those groups to be optionally substituted by one or more identical or different groups selected from halogen atoms, linear or branched ($C_1$–$C_6$) alkyl groups, hydroxy groups, linear or branched ($C_1$–$C_6$) alkoxy groups, nitro groups, cyano groups, linear or branched trihalo-($C_1$–$C_6$)alkyl groups, amino groups, monoalkylamino groups in which the alkyl moiety has from 1 to 6 carbon atoms and is linear or branched and dialkylamino groups in which each alkyl moiety has from 1 to 6 carbon atoms and is linear or branched.

"Heteroaryl group" is understood to mean an aryl group as defined hereinbefore, containing within the ring system from one to three identical or different hetero atoms selected from oxygen, nitrogen and sulphur, said heteroaryl group being optionally substituted by one or more identical or different groups selected from the substituents defined above for the aryl group. Among the heteroaryl groups there may be mentioned by way of non-limiting example the groups pyridyl, pyrimidinyl, indolyl, benzofuranyl, benzothienyl, quinolyl, isoquinolyl, benzo[1,4]dioxinyl, 2,3-dihydrobenzo [1,4]dioxinyl, etc.

"Cycloalkyl group" is understood to mean a mono- or poly-cyclic system, having from 3 to 12 ring members, optionally containing one or more unsaturations, which do not confer an aromatic character upon the said ring system.

"Heterocycloalkyl group" is understood to mean a cycloalkyl group as defined hereinbefore, containing within the ring system from one to three identical or different hetero atoms selected from oxygen, nitrogen and sulphur.

Preferred compounds of the invention are the compounds of formula (I) wherein n has the value 1.

Preferred $R_1$ and $R_2$ substituents according to the invention are the hydrogen atom, the linear or branched ($C_1$–$C_6$) alkyl group, and the group 2,3-dihydro-1,4-benzodioxin-2-ylmethyl.

A preferred substituent T according to the invention is the saturated monocyclic ($C_3$–$C_8$)cycloalkyl group.

Advantageously, preferred substituents T according to the invention are the cyclopentyl and cyclohexyl groups.

According to an advantageous embodiment of the invention, preferred compounds of the invention are the compounds of formula (I/A):

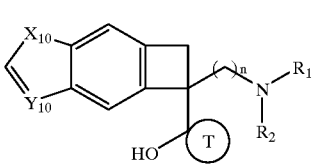
(I/A)

wherein n, $R_1$, $R_2$ and T are as defined for formula (I), $X_{10}$ represents an oxygen atom or a sulphur atom, and $Y_{10}$ represents a CH group.

According to another advantageous embodiment of the invention, preferred compounds of the invention are the compounds of formula (I/B):

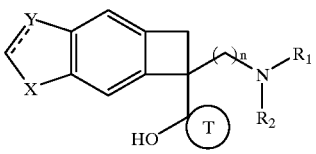
(I/B)

wherein X, Y, n, $R_1$, $R_2$, $R_3$ and T are as defined for formula (I).

Advantageously, preferred compounds of the invention are the compounds of formula (I/B) wherein n is 1, and X represents a group $NR_3$ wherein $R_3$ represents a hydrogen atom or a linear or branched ($C_1$–$C_6$)alkyl group.

According to a third advantageous embodiment of the invention, preferred compounds of the invention are the compounds of formula (I/C):

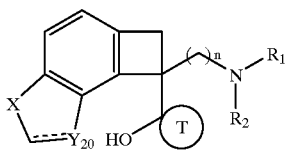
(I/C)

wherein n, $R_1$, $R_2$, X and T are as defined for formula (I), and $Y_{20}$ represents a CH or $CH_2$ group.

According to a fourth advantageous embodiment of the invention, preferred compounds of the invention are the compounds of formula (I/D):

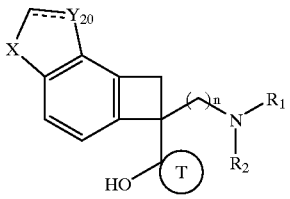
(I/D)

wherein n, $R_1$, $R_2$, X and T are as defined for formula (I), and $Y_{20}$ represents a CH or $CH_2$ group.

According to another advantageous embodiment of the invention, preferred compounds of the invention are the compounds of formula (I/E):

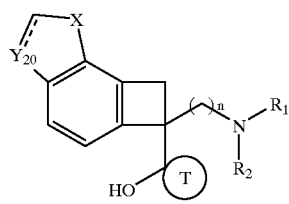
(I/E)

wherein n, $R_1$, $R_2$, X and T are as defined for formula (I), and $Y_{20}$ represents a CH or $CH_2$ group.

Lastly, according to a final valuable embodiment of the invention, preferred compounds of the invention are the compounds of formula (I/F):

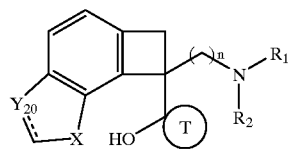
(I/F)

wherein n, $R_1$, $R_2$, X and T are as defined for formula (I), and $Y_{20}$ represents a CH or $CH_2$ group.

Preferred compounds of the invention are:
- 1-{6-[(dimethylamino)methyl]-1-methyl-2,3,5,6-tetrahydro-1H-cyclobuta[f]indol-6-yl}cyclohexanol,
- 1-{6-[(dimethylamino)methyl]-2,3,5,6-tetrahydro-1H-cyclobuta[f]indol-6-yl}cyclohexanol,
- 1-{5-[(dimethylamino)methyl]-5,6-dihydrocyclobuta[f][1]benzofuran-5-yl}cyclohexanol,
- 1-{5-[(dimethylamino)methyl]-5,6-dihydrocyclobuta[f][1]benzothien-5-yl}cyclohexanol,
- 1-{6-[(dimethylamino)methyl]-1-methyl-5,6-dihydro-1H-cyclobuta[f]indol-6-yl}cyclohexanol,
- 1-{7-[(dimethylamino)methyl]-2,3,6,7-tetrahydro-1H-cyclobuta[e]indol-7-yl}cyclohexanol,
- 1-{5-[(methylamino)methyl]-5,6-dihydrocyclobuta[f][1]benzothien-5-yl}cyclopentanol,
- 1-{5-[(dimethylamino)methyl]-5,6-dihydrocyclobuta[f][1]benzothien-5-yl}cyclopentanol,
- (+)-1-{5-[(dimethylamino)methyl]-5,6-dihydrocyclobuta[f][1]benzothien-5-yl}cyclopentanol,
- (−)-1-{5-[(dimethylamino)methyl]-5,6-dihydrocyclobuta[f][1]benzothien-5-yl}cyclopentanol,
- 1-{6-[(dimethylamino)methyl]-5,6-dihydrocyclobuta[f][1]benzothien-6-yl}cyclopentanol,
- 1-{5-[(dimethylamino)methyl]-1-methyl-5,6-dihydro-1H-cyclobuta[f]indol-5-yl}cyclopentanol,
- 1-{7-[(dimethylamino)methyl]-6,7-dihydrocyclobuta[g][1]benzofuran-7-yl}cyclopentanol,
- 1-{1-[(dimethylamino)methyl]-1,2-dihydrocyclobuta[b]naphthalen-1-yl}cyclopentanol,
- 1-{7-[(dimethylamino)methyl]-6,7-dihydro-3H-cyclobuta[e]indol-7-yl}cyclopentanol,
- 1-{1-[(dimethylamino)methyl]-1,2-dihydrocyclobuta[a]naphthalen-1-yl}cyclopentanol.

The isomers and addition salts with a pharmaceutically acceptable acid or base of the preferred compounds form an integral part of the invention.

Isomers are understood to be the optical isomers, such as the diastereoisomers and enantiomers.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The present invention relates also to a process for the preparation of compounds of formula (I), characterised in that there is used as starting material:

a) either a compound of formula (II):

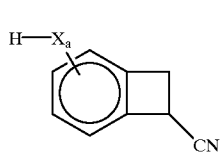
(II)

wherein $X_a$ represents a sulphur atom, an oxygen atom, or an NH group, which compound of formula (II) is reacted with a compound of formula (III):

    (III)

wherein A represents a linear or branched $(C_1-C_4)$alkyl group and Z represents a formyl group (when $X_a$ represents an NH group), or a group —$CH_2$Hal wherein Hal represents a chlorine, bromine or iodine atom, to yield compounds of formula (IV):

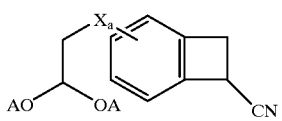
(IV)

wherein $X_a$ and A are as defined hereinbefore,
which compounds of formula (IV) are subjected:
either, when $X_a$ has the meaning $X_1$ representing an oxygen atom or a sulphur atom, to conditions of cyclisation by the action of an acid, such as polyphosphoric acid or a Lewis acid, to yield compounds of formula (V/a):

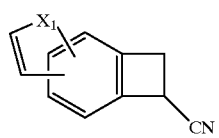
(V/a)

wherein $X_1$ represents an oxygen atom or a sulphur atom, which compounds of formula (V/a) are treated:
either, in the presence of a strong base, with a cyclic ketone of formula (VI):

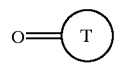
(VI)

wherein T has the same meanings as for formula (I),
to yield compounds of formula (VII/a),

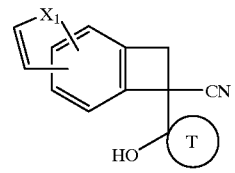
(VII/a)

wherein $X_1$ and T are as defined hereinbefore,
which compounds of formula (VII/a) are subjected to the action of a reducing agent according to conventional conditions of organic synthesis, to yield compounds of formula (I/a), a particular case of the compounds of formula (I):

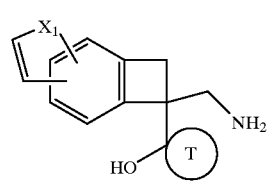
(I/a)

wherein $X_1$ and T are as defined hereinbefore,
for which compounds of formula (I/a):
either the primary amine function is substituted according to conventional methods of organic synthesis, such as reductive amination or nucleophilic substitution with a compound of formula (VIIIa):

    (VIIIa)

wherein $R'_1$ has the same meanings as $R_1$ for formula (I) with the exception of the meaning of a hydrogen atom, and $Z_1$ represents a leaving group customary in organic chemistry, such as a halogen atom or a mesylate or tosylate group, to yield compounds of formula (I/b$_1$), a particular case of the compounds of formula (I):

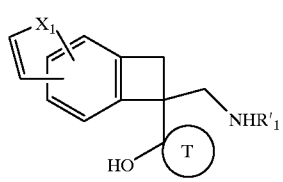
(I/b$_1$)

wherein $X_1$, T and $R'_1$ are as defined hereinbefore,
or according to an advantageous embodiment of the process, treatment is carried out with a compound of formula (VIIIb):

    (VIIIb)

wherein $R''_1$ represents a heterocycloalkyl-$(C_1-C_5)$alkyl group in which the alkyl moiety is linear or branched, and $Z_2$ represents a chlorine atom or an imidazolyl group, to yield compounds of formula (I/b$_2$):

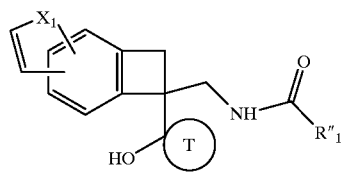

(I/b$_2$)

wherein $X_1$, T and $R''_1$ are as defined hereinbefore,
which compounds of formula (I/b$_2$) are reduced with a reducing agent conventionally used in organic chemistry, to yield compounds of formula (I/b$_3$):

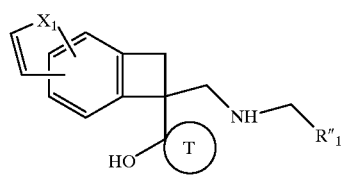

(I/b$_3$)

wherein $X_1$, $R''_1$ and T are as defined hereinbefore,
the totality of the compounds of formulae (I/b$_1$) and (I/b$_3$) constituting the compounds of formula (I/b),
which compounds of formula (I/b) are treated according to the same conditions as those described hereinbefore with a compound of formula (VIIIc):

$R'_2$—$Z_1$ (VIIIc)

wherein $Z_1$ is as defined hereinbefore and $R'_2$ has the same meanings as $R_2$ for formula (I) with the exception of the meaning of a hydrogen atom,
to yield compounds of formula (I/c), a particular case of the compounds of formula (I):

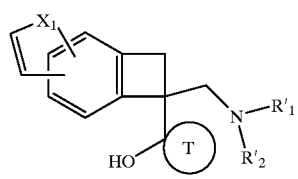

(I/c)

wherein $X_1$, T, $R'_1$ and $R'_2$ are as defined hereinbefore,
or, in the presence of a strong base, with an amine of formula (IX):

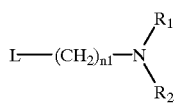

(IX)

wherein $R_1$ and $R_2$ are as defined for formula (I), $n_1$ is an integer from 2 to 6 inclusive, and L represents a leaving group, such as a halogen atom, or a mesylate, tosylate or trifluoromethanesulphonate group, to yield compounds of formula (X):

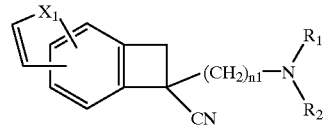

(X)

wherein $X_1$, $n_1$, $R_1$ and $R_2$ are as defined hereinbefore, which compounds of formula (X) are treated with hydrogen peroxide in the presence of sodium carbonate, to yield compounds of formula (XI):

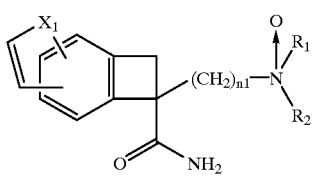

(XI)

wherein $X_1$, $n_1$, $R_1$ and $R_2$ are as defined hereinbefore, which compounds of formula (XI) are reduced by the action of ammonium formate in the presence of 10% Pd/C, to yield compounds of formula (XII):

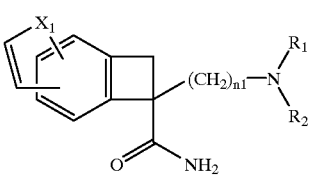

(XII)

wherein $X_1$, $n_1$, $R_1$ and $R_2$ are as defined hereinbefore, which compounds of formula (XII) are subjected to the action of a compound of formula (XIII):

$(CH_3)_2N$—$CH(OG)_2$ (XIII)

wherein G represents a linear or branched $(C_1$–$C_6)$alkyl group, a benzyl group or a cyclohexyl group,
to yield compounds of formula (XIV):

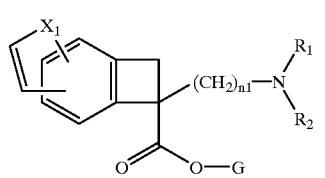

(XIV)

wherein $X_1$, $n_1$, $R_1$ and $R_2$ are as defined hereinbefore, which compounds of formula (XIV) are treated with a dimagnesium compound of formula (XV):

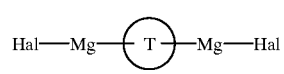

(XV)

wherein Hal represents a halogen atom, and T is as defined for formula (I),
to yield compounds of formula (I/d), a particular case of the compounds of formula (I):

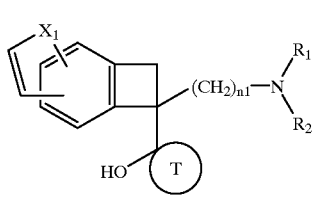

(I/d)

wherein $X_1$, $n_1$, $R_1$, $R_2$ and T are as defined hereinbefore, the totality of the compounds of formulae (I/a), (I/b), (I/c) and (I/d), in the particular case when $X_1$ represents a sulphur atom, constituting the compounds of formula (I/e):

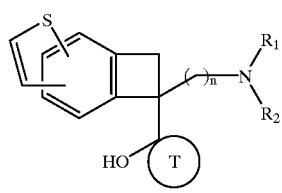

(I/e)

wherein n, $R_1$, $R_2$ and T are as defined for formula (I), which compounds of formula (I/e) are subjected to the action of an oxidising agent according to conventional conditions of organic synthesis, to yield compounds of formula (I/f), a particular case of the compounds of formula (I):

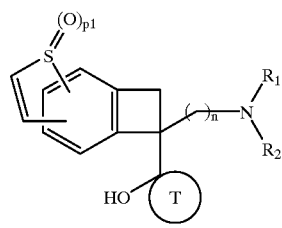

(I/f)

wherein $p_1$ is an integer selected from 1 and 2, and n, $R_1$, $R_2$ and T are as defined hereinbefore,
the totality of the compounds of formulae (I/a), (I/b), (I/c), (I/d) (wherein $X_1$ represents an oxygen or sulphur atom) and (I/f) constituting the compounds of formula (I/g):

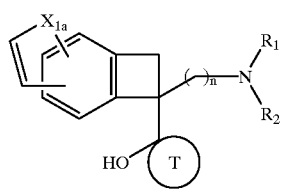

(I/g)

wherein $X_{1a}$ represents an oxygen atom or a group of formula $S(O)_p$ wherein p is as defined for formula (I), and n, $R_1$, $R_2$ and T are as defined for formula (I),
which compounds of formula (I/g) are subjected to the action of a reducing agent according to conventional conditions of organic synthesis, to yield compounds of formula (I/h), a particular case of the compounds of formula (I):

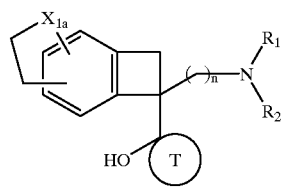

(I/h)

wherein $X_{1a}$, n, $R_1$, $R_2$ and T are as defined hereinbefore,
or, when $X_a$ has the meaning $X'_2$ representing an NH group, to the action of a sulphonic acid chloride of formula (XVI):

$$E-SO_2Cl \qquad (XVI)$$

wherein E represents a linear or branched $(C_1-C_4)$alkyl group, a phenyl group or a p-toluyl group,
to yield compounds of formula (XVII):

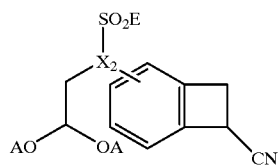

(XVII)

wherein $X_2$ represents a nitrogen atom, and E and A are as defined hereinbefore,
which compounds of formula (XVII) are cyclised by the action of an acid to yield compounds of formula (V/b):

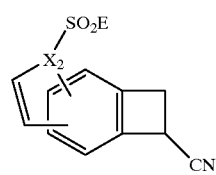

(V/b)

wherein $X_2$ and E are as defined hereinbefore,
the cyclic amine of which compounds of formula (V/b) is deprotected by the action of a basic agent, which are then subjected to the action of a reducing agent according to conventional conditions of organic synthesis, to yield compounds of formula (V/c):

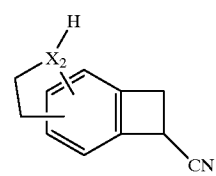

(V/c)

wherein $X_2$ is as defined hereinbefore,
which compounds of formula (V/c) are subjected to the action of a compound of formula (VI) as described hereinbefore to yield compounds of formula (VII/b):

(VII/b)

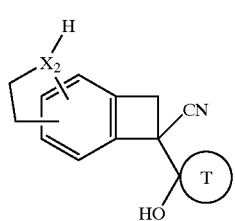

wherein $X_2$ is as defined hereinbefore and T is as defined for formula (I), which compounds of formula (VII/b) are:

either treated according to the same conditions as those described for the compounds of formula (VII/a), to yield compounds of formula (I/i), a particular case of the compounds of formula (I):

(I/i)

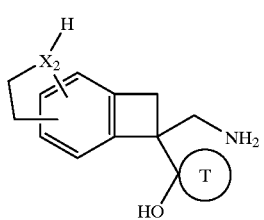

wherein $X_2$ and T are as defined hereinbefore, which compounds of formula (I/i) may be treated in succession with a compound of formula (VIIIa) or (VIIIb), and then (VIIIc), as defined hereinbefore, to yield compounds of formulae (I/j) and (I/k), respectively, particular cases of the compounds of formula (I):

(I/j)

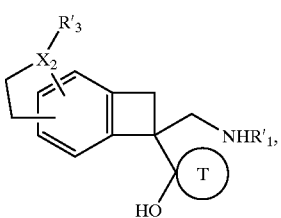

(I/k)

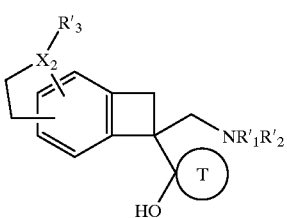

wherein $X_2$, T, $R'_1$ and $R'_2$ are as defined hereinbefore, and $R'_3$ has the same meanings and values as $R'_1$, the totality of the compounds of formulae (I/i), (I/j) and (I/k) constituting the compounds of formula (I/l):

(I/l)

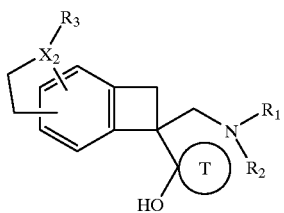

wherein $X_2$, $R_1$, $R_2$, $R_3$ and T are as defined for formula (I), which compounds of formula (I/l) are subjected to the action of an oxidising agent, such as manganese dioxide, to yield compounds of formula (I/m), a particular case of the compounds of formula (I):

(I/m)

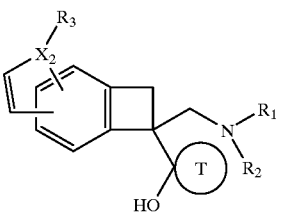

wherein $X_2$, $R_1$, $R_2$, $R_3$ and T are as defined hereinbefore, or treated with a compound of formula (XVI) as defined hereinbefore, to yield compounds of formula (XVIII):

(XVIII)

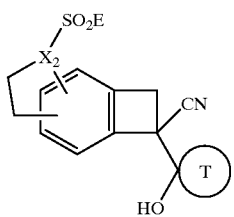

wherein T, $X_2$ and E are as defined hereinbefore, which compounds of formula (XVIII) are reduced according to conventional conditions of organic synthesis, to yield compounds of formula (XIX):

(XIX)

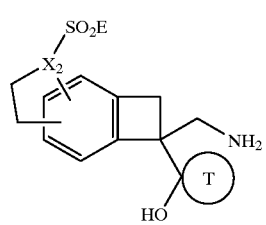

wherein T, $X_2$ and E are as defined hereinbefore, the primary amine function of which compounds of formula (XIX) may be substituted by the action of a compound of formula ($VIII_a$) as defined hereinbefore, to yield compounds of formula (XX):

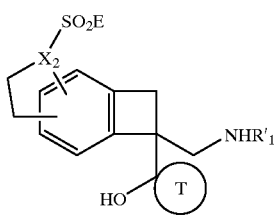

(XX)

wherein T, $X_2$, E and $R'_1$ have the same meanings as those described hereinbefore,
which compounds of formula (XX) may be converted into tertiary amines by the action of a compound of formula ($VIII_b$) as defined hereinbefore, to yield compounds of formula (XXI):

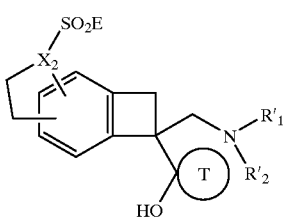

(XXI)

wherein T, $X_2$, E, $R'_1$ and $R'_2$ are as defined hereinbefore, which compounds of formulae (XX) and (XXI) are then deprotected by treatment with sodium in liquid ammonia, to yield compounds of formulae (I/n) and (I/o), respectively, particular cases of the compounds of formula (I):

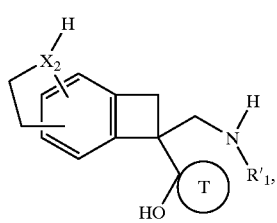

(I/n)

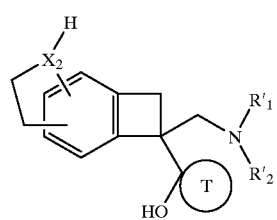

(I/o)

wherein T, $X_2$, $R'_1$ and $R'_2$ are as defined hereinbefore,
b) or a compound of formula (II/1):

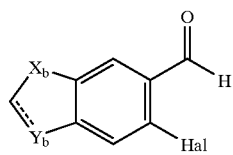

(II/1)

wherein Hal represents a halogen atom, and $X_b$ represents an oxygen atom when $Y_b$ represents an oxygen atom and ----- denotes a single bond, or $X_b$ represents a group —CH=CH— when $Y_b$ represents a CH group and ----- denotes a double bond, which compounds of formula (II/1) are reacted with (EtO)$_2$POCH$_2$CN to yield compounds of formula (II/2):

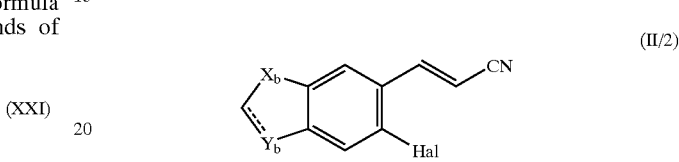

(II/2)

wherein Hal, $X_b$ and $Y_b$ are as defined hereinbefore,
which compounds of formula (II/2) are first subjected to the action of a reducing agent conventional in organic chemistry and then reacted with NaNH$_2$, to yield compounds of formula (II/3):

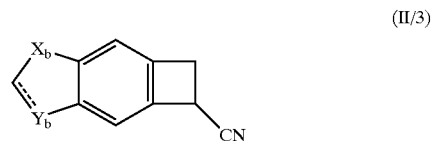

(II/3)

wherein Xb and Yb are as defined hereinbefore,
which compounds of formula (II/3) may be treated under the same conditions as the compounds of formula (V/a), either with a compound of formula (VI), then (VIIIa) or (VIIIb), and then (VIIIc), to yield, in succession, compounds of formulae ($I/3_a$), ($I/3_b$) and ($I/3_c$):

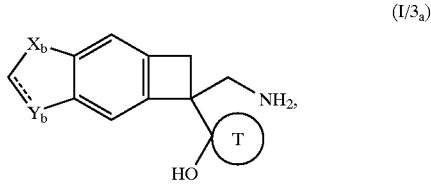

($I/3_a$)

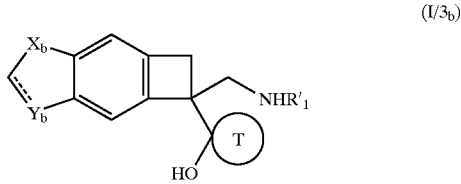

($I/3_b$)

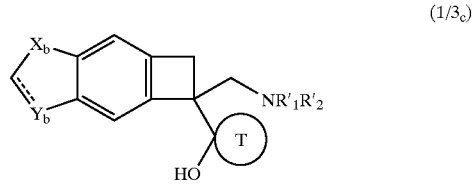

($I/3_c$)

wherein $X_b$, $Y_b$, T, $R'_1$ and $R'_2$ are as defined hereinbefore, or with a compound of formula (IX), the resulting product then being treated in the same manner as the compounds of formulae (X) and (XI), and then subjected to the successive action of a compound of formula (XIII) then (XV), as described hereinbefore, to yield compounds of formula (I/3$_d$):

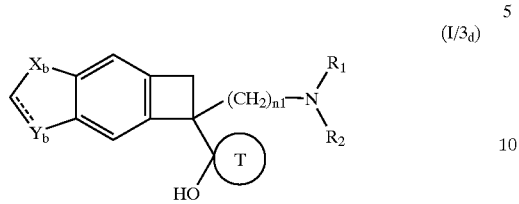

(I/3$_d$)

wherein $X_b$, $Y_b$, $n_1$, $R_1$ and $R_2$ are as defined hereinbefore, which compounds (I/a) to (I/o) and (I/3$_a$) to (I/3$_d$) constitute the totality of the compounds of the invention, which are purified, if necessary, according to a conventional purification technique, which may be separated, if desired, into their different isomers according to a conventional separation technique, and which are converted, where appropriate, into their addition salts with a pharmaceutically acceptable acid or base.

The compounds of formulae (II), (II/1), (III), (VI), (VIIIa), (VIIIb), (VIIIc), (IX), (XIII), (XV) and (XVI) are either known products or are obtained starting from known substances according to conventional processes of organic chemistry.

The compounds of the present invention are inhibitors of serotonin, noradrenalin and dopamine reuptake. They are useful as medicaments in the treatment of depression, panic attacks, obsessive-compulsive disorders, phobias, impulsive disorders, drug abuse, anxiety, obesity and bulimia.

The present invention relates also to pharmaceutical compositions comprising as active ingredient at least one compound of formula (I), an optical isomer, or an addition salt thereof with a pharmaceutically acceptable acid or base, alone or in combination with one or more inert, non-toxic pharmaceutically acceptable excipients or carriers.

Among the pharmaceutical compositions according to the invention, there may be mentioned more especially those that are suitable for oral, parenteral (intravenous, intramuscular or subcutaneous), per- or trans-cutaneous, nasal, rectal, perlingual, ocular or respiratory administration, and especially tablets or dragées, sublingual tablets, soft gelatin capsules, hard gelatin capsules, suppositories, creams, ointments, dermal gels, injectable or drinkable preparations, aerosols, eye or nose drops, etc.

The useful dosage varies according to the age and weight of the patient, the route of administration, the nature and severity of the disorder, and whether any associated treatments are being taken and ranges from 0.5 mg to 25 mg in one or more administrations per day.

The following Examples illustrate the invention but do not limit it in any way. The starting materials used are known products or are prepared according to known procedures. The various Preparations yield synthesis intermediates for use in the preparation of the compounds of the invention.

The structures of the compounds described in the Examples were determined according to the usual spectrophotometric techniques (infrared, nuclear magnetic resonance, mass spectrometry, etc.).

The melting points were determined using a Kofler hot plate (K.), or using a hot plate under a microscope (M.K.). When the compound is present in the form of a salt, the melting point given corresponds to that of the salt product.

By way of information, the numbering adopted for the various tricyclic systems is as follows:

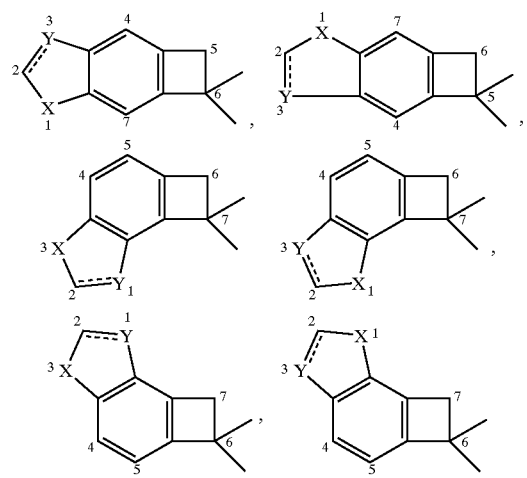

PREPARATION 1

6-Cyano-1-methylsulphonyl-5,6-dihydrocyclobuta[f]indole

Step 1

1-Cyano-5-[(2,2-dimethoxyethyl)amino]benzocyclobutane

To a suspension of 13.5 g of 1-cyano-5-aminobenzocyclobutane in 400 ml of 1,2-dichloroethane there are added rapidly, dropwise, 26.5 ml of a 45% solution of 2,2-dimethoxyacetaldehyde in tert-butyl methyl ether, then 16 ml of acetic acid and finally, in fractions, 39.7 g of sodium triacetoxyborohydride. After increasing the temperature to 29° C., the mixture is cooled again to room temperature, and then stirred for 1 hour 15 minutes and hydrolysed by pouring into 500 ml of an aqueous saturated sodium hydrogen carbonate solution. The organic phase is separated off, washed with water and concentrated under reduced pressure to yield the desired product in a quantitative yield.

Step 2

1-Cyano 5-[(N-(2,2-dimethoxyethyl)-N-methylsulphonylamino]benzocyclobutane

A solution prepared starting from 21.6 g of the product obtained in the preceding Step 1, 58 ml of pyridine and 225 ml of dichloromethane is cooled to 0° C. 10.8 ml of mesyl chloride are added dropwise over the course of 20 minutes and stirring is carried out for a further 40 minutes at 0° C. and then for 20 hours at room temperature. The reaction mixture is then poured into 40 ml of an aqueous saturated sodium hydrogen carbonate solution. After decanting, the aqueous phase is extracted twice with 150 ml of methylene chloride each time. The combined organic phases are washed with 1N hydrochloric acid, dried and concentrated to yield the expected product in a quantitative yield.

Step 3

6-Cyano-1-methylsulphonyl-5,6-dihydrocyclobuta[f]indole

A solution of 10.9 ml of titanium chloride in 450 ml of toluene and a solution of 27.9 g of the product obtained in Step 2 diluted in 450 ml of toluene are poured simultaneously over the course of 1 hour 15 minutes into 2.1 liters of toluene at reflux. When the addition is complete, the temperature is left to drop to 40° C., and the mixture is poured into 1.8 liters of an aqueous saturated sodium hydrogen carbonate solution. After decanting, the aqueous phase is extracted with toluene, and the organic phases are combined, washed, dried and concentrated. The residue is purified by chromatography over silica gel (dichloromethane/cyclohexane: 75/25) to yield the expected product and its regioisomer.

Melting point: 142–144° C. (MK)

PREPARATION 2

6-Cyano-5,6-dihydrocyclobuta[f]indole 2.6 g of the product of Preparation 1 are introduced into a solution of 7.7 g of potassium hydroxide in 190 ml of methanol. After 12 hours at reflux, the methanol is removed by evaporation and the residue is taken up in ether. After washing, the organic phase is dried and concentrated to yield the expected product.

Melting point: 126–128° C. (MK)

PREPARATION 3

6-Cyano-2,3,5,6-tetrahydrocyclobuta[f]indole 3.43 g of the product obtained in Preparation 2 are dissolved in 55 ml of acetic acid. 3.84 g of sodium cyanoborohydride are added in portions over the course of 5 minutes to the reaction mixture which has been cooled to 13° C. After returning to room temperature, stirring is maintained for 2 hours, and then the reaction mixture is cooled to 0° C. and brought to pH=11 by the addition of a sodium hydroxide solution (45 g in 250 ml of water). The resulting milky solution is extracted with ether. The organic phases are washed, dried and concentrated to yield the expected product in the form of a white solid.

Melting point: 85–87° C. (MK)

PREPARATION 4

4-Cyano-1-methylsulphonyl-4,5-dihydrocyclobuta[f]indole

The regioisomer obtained in Step 3 of Preparation 1 corresponds to the expected product.

Melting point: 118–120° C. (MK)

PREPARATION 5

4-Cyano-4,5-dihydrocyclobuta[e]indole

The product is obtained according to the process of Preparation 2, using the product of Preparation 4 as substrate.

Melting point: 132–134° C. (MK)

PREPARATION 6

4-Cyano-2,3,4,5-tetrahydrocyclobuta[e]indole

The product is obtained according to the process of Preparation 3, using the product of Preparation 5 as substrate.

PREPARATION 7

5-Cyano-5,6-dihydrocyclobuta[f]benzothiophene

Step 1

1-Cyano-4-thiomethylbenzocyclobutane

Into 3.5 liters of liquid ammonia at reflux containing catalytic amounts of potassium ferrocyanide and iron trinitrate monohydrate there are introduced, over the course of 2 hours, 50.8 g of sodium, followed, over the course of 5 minutes, by 153 g of 3-(2-chloro-5-thiomethylphenyl) propionitrile. The mixture is left to react for 1 hour at –33° C. and then 118.2 g of solid ammonium chloride are introduced. After removal of the ammonia by evaporation, the residue is taken up in ether, the salts are filtered off and the filtrate is evaporated to dryness, enabling the expected product to be obtained.

Step 2

1-Cyano-4-methylsulphinylbenzocyclobutane 11 g of the product of the preceding Step 1 are dissolved in 70 ml of dichloromethane. Onto the solution, which has been cooled to –5° C., there is poured a solution of 15.8 g of m-chloroperbenzoic acid in 80 ml of dichloromethane. After 10 minutes' stirring, the reaction mixture is poured into 100 ml of water and 100 ml of 1N sodium hydroxide solution. Decanting is carried out, and the aqueous phase is extracted again with dichloromethane. The combined organic phases are washed with sodium hydrogen sulphate, and then with 1N sodium hydroxide solution, with sodium hydrogen carbonate and finally with water until neutral. The organic phase is dried and concentrated to yield the expected product.

Step 3

1-Cyano-4-mercaptobenzocyclobutane 9.76 ml of trifluoroacetic acid dissolved in 20 ml of dichloromethane are added to a solution of 11 g of the product obtained in the preceding Step in 100 ml of dichloromethane. The addition lasts for 45 minutes, during which time the temperature is maintained at 25° C. The reaction mixture is stirred again for 1 hour 30 minutes at that temperature, and then evaporated to dryness. The residue is taken up by stirring for 10 minutes in the presence of a 50/50 mixture of triethylamine and methanol. After evaporation, the residue is diluted with dichloromethane, washed with a saturated ammonium chloride solution and then with water, dried and concentrated to obtain the expected product in the form of an oil.

Step 4

1-Cyano-4-(2,2-diethoxyethylsulphanyl) benzocyclobutane 3.65 g of sodium borohydride are added in portions, at 20° C., to a solution of 9.1 g of the product obtained in the preceding Step 3 in 20 ml of tetrahydrofuran and 140 ml of ethanol. After 1 hour at 50° C., 2.14 g of solid sodium borohydride are added again. The reaction mixture is then heated to 80° C. and, at that temperature, 39 ml of bromoacetaldehyde diethylacetal are poured in over the course of 1 hour. Heating is maintained for a further 12 hours, and then the cooled reaction mixture is poured into 1 liter of ice-cold water. The resulting mixture is extracted with ether and the organic phase is washed with a 10% sodium hydrogen carbonate solution and then with water. The ethereal phase is dried and concentrated in vacuo to yield the expected product in the form of an oil.

Step 5

5-Cyano-5,6-dihydrocyclobuta[f]benzothiophene 10 g of polyphosphoric acid, and 8.5 g of the product obtained in the preceding Step 4 in 500 ml of chlorobenzene are heated at 130° C. for 4 hours. After cooling, the supernatant is drawn off and the residue is rinsed with dichloromethane. The supernatant and the dichloromethane phase are combined and neutralised by adding powdered sodium hydrogen carbonate. After 15 minutes' stirring, filtration is carried out, followed by evaporation to dryness. The residue is purified by chromatography over silica gel (cyclohexane/dichloromethane: 50/50), enabling the expected product and a by-product to be obtained.

Melting point: 102–103° C. (MK)

PREPARATION 8

6-Cyano-5,6-dihydrocyclobuta[f]benzothiophene

The product is obtained according to the process of Preparation 7, Steps 1 to 5, but in Step 1 using 3-(3-bromo-4-thiomethylphenyl)propionitrile instead of 3-(2-chloro-5-thiomethylphenyl)propionitrile.

PREPARATION 9

5-Cyano-5,6-dihydrocyclobuta[f]benzofuran

Step 1

1-Cyano-4-(2,2-diethoxyethoxy)benzocyclobutane

A solution of 16.5 g of 1-cyano-4-hydroxybenzocyclobutane in 205 ml of dimethylformamide is poured into a suspension of 67.8 mmol of sodium hydride in 160 ml of dimethylformamide. The reaction mixture is stirred for 30 minutes and then a solution of 10.2 ml of 1-bromo-2,2-diethoxyethane in 40 ml is added over the course of 15 minutes and the temperature is then maintained at 60° C. for 6 hours. The mixture is stirred for a further 12 hours, the dimethylformamide is removed by evaporation, and the residue is taken up in water, extracted with dichloromethane, dried and concentrated in vacuo. The residue is chromatographed over silica gel (CH$_2$Cl$_2$/AcOEt: 95/5), enabling the expected product to be isolated.

Step 2

5-Cyano-5,6-dihydrocyclobuta[f]benzofuran

The product is obtained as in Step 3 of Preparation 1, but using the product of the preceding Step 1. In the course of chromatography over silica gel (CH$_2$Cl$_2$/cyclohexane: 80/20), the expected product and a by-product are isolated.

PREPARATION 10

6-Cyano-5,6-dihydrocyclobuta[f]benzofuran

The product is obtained in the same manner as the product of Preparation 9, but in Step 1 using 1-cyano-5-hydroxybenzocyclobutane and in Step 2 using the mixture CH$_2$Cl$_2$/cyclohexane: 75/25 as eluant for the separation of the regioisomers. The expected product is isolated in the form of an oil.

PREPARATION 11

5-Cyano-4,5-dihydrocyclobuta[e]benzothiophene

The by-product obtained in Step 5 of Preparation 7 corresponds to the expected product.

PREPARATION 12

4-Cyano-4,5-dihydrocyclobuta[e]benzothiophene

The product is obtained in the course of Step 5 of Preparation 8.

PREPARATION 13

5-Cyano-4,5-dihydrocyclobuta[e]benzothiophene

The by-product obtained in Step 2 of Preparation 9 corresponds to the expected product.

PREPARATION 14

4-Cyano-4,5-dihydrocyclobuta[e]benzofuran

The by-product isolated in the course of the chromatography of Preparation 10 corresponds to the expected product.

PREPARATION 15

5,6-Dihydrocyclobuta[f][1,3]benzodioxole-5-carbonitrile 46 g of 3-(6-bromo-1,3-benzodioxol-5-yl)propanenitrile are introduced in portions into 1.4 liters of liquid ammonia in which there is dissolved sodium azide which was prepared previously by the introduction of 16.7 g of sodium into the liquid ammonia. After 30 minutes' contact, the reaction mixture is treated with 38.7 g of ammonium chloride, and then the ammonia is distilled off at room temperature. The residue is taken up in ether and filtered; the precipitate is washed with ether. The combined ethereal phases are evaporated and the resulting residue is recrystallised from isopropyl alcohol, enabling the expected product to be isolated.

Melting point: 91° C. (M.K.)

PREPARATION 16

6,7-Dihydrocyclobuta[g][1]benzofuran-7-carbonitrile

Step 1

1-Cyano-6-(2,2-diethoxyethoxy)benzocyclobutane

The product is obtained according to the process of Step 1 of Preparation 9 using 1-cyano-6-hydroxybenzocyclobutane as substrate.

Step 2

6,7-Dihydrocyclobuta[g][1]benzofuran-7-carbonitrile

The product is obtained according to the process of Step 3 of Preparation 1 using the product obtained in the preceding Step 1 as substrate.

PREPARATION 17

1,2-Dihydrocyclobuta[b]naphthalene-1-carbonitrile

The product is obtained according to the process of Preparation 15 using 3-(3-iodo-2-naphthyl)propionitrile as substrate.

Melting point: 98–102° C. (M.K.)

PREPARATION 18

1,2-Dihydrocyclobuta[a]naphthalene-1-carbonitrile

Step 1

1,1-Diethoxy-1,2-dihydrocyclobuta[a]naphthalene 9.4 g of sodium amide are introduced into 350 ml of tetrahydrofuran. 25.9 g of 1-bromonaphthalene and 28 g of freshly prepared 1,1-diethoxyethylene are poured in succession into that mixture. The reaction mixture is refluxed for 16 hours and than taken up in water and ether. After washing the organic phase to neutral pH and drying thereof, the expected product is isolated and chromatographed over silica gel (dichloromethane/cyclohexane: 1/1).

Step 2

Cyclobuta[a]naphthalen-1(2H)-one 10 g of the product obtained in Step 1 are treated at room temperature with 42 ml of 1N hydrochloric acid dissolved in 170 ml of tetrahydrofuran. After 1 hour 30 minutes' contact, the solvent is concentrated and the residue is poured into 170 ml of water. 6.9 g of a solid corresponding to the expected product are then isolated.

Melting point: 92–94° C. (M.K)

Step 3

1,2-Dihydrocyclobuta[a]naphthalen-1-ol 1.4 g of sodium borohydride are added to a suspension, at 0–5° C., of 5.2 g of the product obtained in Step 2 in 150 ml of methanol. After 15 minutes at that temperature and then 1 hour at room temperature, the reaction mixture is poured into 300 g of ice and extracted with dichloromethane. After customary treatment, 5.2 g of the expected product are isolated.

Melting point: 96–100° C. (M.K.)

Step 4

1,2-Dihydrocyclobuta[a]naphthalene-1-carbonitrile 5.1 g of the product obtained in Step 3, 14.2 g of triphenylphosphine, and 12 g of carbon tetrabromide in 150 ml of ether are refluxed for 2 hours. After cooling, the reaction mixture is filtered, concentrated, taken up in 50 ml of ether, filtered and evaporated. The 7.85 g of resulting residue are treated with 10.5 g of tetrabutylammonium cyanide in 150 ml of tetrahydrofuran. After 64 hours' contact at room temperature, the reaction mixture is concentrated and taken up in ice and ether. After decanting, an oil is isolated, which is purified by chromatography over silica gel (dichloromethane), enabling the expected product to be isolated.

Melting point: 78–84° C.

PREPARATION 19

1-(Methylsulphonyl)-5,6-dihydro-1H-cyclobuta[f]indole-5-carbonitrile

The product is obtained according to the process of Preparation 1, Steps 1 to 3, using 4-amino-1-cyanobenzocyclobutane in Step 1.

Melting point: 164–168° C. (M.K.)

PREPARATION 20

5,6-Dihydro-1H-cyclobuta[f]indole-5-carbonitrile

The product is obtained according to the process of Preparation 2 but using the product of Preparation 19 as substrate.

Melting point: 109–113° C. (M.K.)

PREPARATION 21

2,3,5,6-Tetrahydro-1H-cyclobuta[f]indole-5-carbonitrile

The product is obtained according to the process of Preparation 3 but using the product of Preparation 20 as substrate.

Melting point: 100–105° C. (M.K.)

EXAMPLE 1

1-[6-(Aminomethyl)-2,3,5,6-tetrahydro-1H-cyclobuta[f]indol-6-yl]cyclohexanol

Step A 6-(1-Hydroxycyclohexyl)-2,3,5,6-tetrahydro-1H-cyclobuta[f]indole-6-carbonitrile 4.1 g of the product obtained in Preparation 3 are dissolved in 215 ml of tetrahydrofuran. The reaction mixture is cooled to −80° C. and 19.25 ml of a 2.5M solution of n-butyllithium in hexane are added. When the addition is complete, stirring is maintained for 20 minutes and then 6.2 ml of cyclohexanone are poured in over the course of 3 minutes. After 2 hours' contact at 80° C., the reaction mixture is left to return to room temperature, and 23 ml of an aqueous saturated ammonium chloride solution, and then 135 ml of water, are introduced. After decanting, the organic phase is washed with a saturated sodium chloride solution, dried and concentrated. The resulting residue is solidified with isopropyl ether and filtered to obtain the desired product, and the filtrate is purified by chromatography over silica gel ($CH_2Cl_2$/AcOEt: 90/10) to isolate an additional amount of the expected product.

Melting point: 168–170° C.

Step B

1-[6-(Aminomethyl)-2,3,5,6-tetrahydro-1H-cyclobuta[f]indol-6-yl]cyclohexanol 4 g of the product obtained in the preceding Step A are dissolved in 200 ml of a 3.6N solution of ammoniacal methanol containing 2 ml of Raney nickel. The reaction mixture is hydrogenated under a pressure of 30 bars at 60° C. for 24 hours. After filtration and removal of the solvent by evaporation, the residue is taken up in dichloromethane, washed with water until neutral, dried and concentrated to isolate the expected product in the form of an oil.

EXAMPLE 2

1-{6-[(Dimethylamino)methyl]-1-methyl-2,3,5,6-tetrahydro-1H-cyclobuta[f]indol-6-yl}cyclohexanol 659 mg of the product of Example 1 are dissolved in 20 ml of acetonitrile. Into that solution, which has been cooled to 0° C., there are introduced 608 mg of sodium cyanoborohydride and 1.5 ml of a 37% solution of formaldehyde in water, whilst maintaining the temperature at 0° C. After 20 hours at room temperature, hydrolysis is carried out with 33 ml of 1N hydrochloric acid and stirring is carried out for 3 hours. The reaction mixture is washed with 30 ml of ether and then rendered basic with 20% sodium hydroxide solution. The aqueous phase is extracted with dichloromethane. After drying and evaporation, the residue is purified by chromatography over silica gel ($CH_2Cl_2$/EtOH: 95/5) to yield the expected product.

Melting point: 121–124° C. (MK)

EXAMPLE 3

1-{6-[(Dimethylamino)methyl]-2,3,5,6-tetrahydro-1H-cyclobuta[f]indol-6-yl}cyclohexanol Step A 6-(1-Hydroxycyclohexyl)-1-(methylsulphonyl)-2,3,5,6-tetrahydro-1H-cyclobuta[f]indole-6-carbonitrile The process is as for Step 2 of Preparation 1 using the product of Step A of Example 1. The expected product is solidified from ether in the form of a violet solid.

Melting point: 174–176° C.

Step B

1-[6-(Aminomethyl)-1-(methylsulphonyl)-2,3,5,6-tetrahydro-1H-cyclobuta[f]indol-6-yl]cyclohexanol The process is as for Step B of Example 1 but using the product of Step A above. The expected product is obtained in the form of a yellow meringue.

Step C

1-[6-[(Dimethylamino)methyl]-1-(methylsulphonyl)-2,3,5,6-tetrahydro-1H-cyclobuta[f]indol-6-yl]cyclohexanol The process is as for Example 2 but using the product of Step B above. The expected product is obtained in the form of a yellow solid.

Melting point: 156–158° C. (MK)

Step D

1-{6-[(Dimethylamino)methyl]-2,3,5,6-tetrahydro-1H-cyclobuta[f]indol-6-yl}cyclohexanol 40 ml of liquid ammonia are introduced into a three-necked flask, followed by 380 mg of the product obtained in Step C dissolved in 10 ml of tetrahydrofuran. The mixture is cooled to −50° C. and 100 mg of sodium are introduced in several portions into the reaction mixture. After 15 minutes' contact, 430 mg of powdered ammonium chloride are introduced in fractions. The reaction mixture is left to return to room temperature. After removal of all the ammonia by evaporation, the residue is taken up in water, extracted with ether, dried and concentrated to obtain the expected product.

Melting point: 159–161° C. (MK)

EXAMPLE 4

1-[5-(Aminomethyl)-5,6-dihydrocyclobuta[f][1]benzofuran-5-yl]cyclohexanol

Step A 5-(1-Hydroxycyclohexyl)-5,6-dihydrocyclobuta[f][1]benzofuran-5-carbonitrile The process is as for Step A of Example 1 but using the product of Preparation 9 and carrying out the hydrolysis of the reaction mixture at −75° C. The expected product is isolated in the form of a solid.

Melting point: 154–158° C. (MK)

Step B

1-[5-(Aminomethyl)-5,6-dihydrocyclobuta[f][1]benzofuran-5-yl]cyclohexanol

A solution of 520 mg of the product obtained in the preceding Step A in 10 ml of tetrahydrofuran is added dropwise at 0° C., under a stream of nitrogen, to a suspension of 177 mg of sodium aluminium hydride in 10 ml of ether. The reaction mixture is stirred for 1 hour at room temperature and then hydrolysed with 0.26 ml of water, 0.79 ml of 20% sodium hydroxide solution and 1.05 ml of water. After 15 minutes' stirring at room temperature, filtration is carried out, followed by evaporation to dryness. The expected product is obtained in the form of a sticky meringue.

EXAMPLE 5

1-{5-[(Dimethylamino)methyl]-5,6-dihydrocyclobuta[f][1]benzofuran-5-yl}cyclohexanol 400 mg of the product of Example 4 are dissolved in 12 ml of acetonitrile. After cooling to 0° C., 0.55 ml of a 37% solution of formaldehyde in water and 185 mg of sodium cyanoborohydride are added in succession. After 1 hour at 0° C. and 2 hours at room temperature, 0.55 ml of 37% solution of formaldehyde in water and 185 mg of sodium cyanoborohydride are added again and stirring is maintained for a further 12 hours at 20° C. Hydrolysis is carried out at room temperature with 22.3 ml of hydrochloric acid (1N) and the mixture is stirred for 1 hour, rendered basic at 0° C. with 20% sodium hydroxide solution, extracted with dichloromethane, washed with water, dried and concentrated. Chromatography over silica gel ($CH_2Cl_2$/EtOH: 90/10) enables the expected product to be isolated in the form of white crystals.

Melting point: 127–136° C. (M.K)

EXAMPLE 6

1-[5-(Aminomethyl)-5,6-dihydrocyclobuta[f][1]benzothien-5-yl]cyclohexanol

The process is as for Example 4, Steps A to B, using the product of Preparation 7 in Step A.

EXAMPLE 7

1-{5-[(Dimethylamino)methyl]-5,6-dihydrocyclobuta[f][1]benzothien-5-yl}cyclohexanol The process is as for Example 5 using the product of Example 6 as substrate.

Melting point: 151–155° C. (MK)

EXAMPLE 8

1-{6-[(Dimethylamino)methyl]-1-methyl-5,6-dihydro-1H-cyclobuta[f]indol-6-yl}cyclohexanol 0.44 g of the product of Example 1 and 1.23 g of manganese dioxide are introduced into 15 ml of toluene. The reaction mixture is stirred for 24 hours at room temperature and then 0.6 g of manganese dioxide is added again, stirring being maintained for a further 24 hours. After filtration over Celite and removal of the solvent by evaporation, the residue is purified by rapid chromatography over silica gel ($CH_2Cl_2$/MeOH/$NH_4OH$: 98/20/0.2%) to yield the expected product.

Melting point: 148–150° C. (MK)

EXAMPLE 9

1-{7-[(Dimethylamino)methyl]-2,3,6,7-tetrahydro-1H-cyclobuta[e]indol-7-yl}cyclohexanol Step A 7-(1-Hydroxycyclohexyl)-2,3,6,7-tetrahydro-1H-cyclobuta[e]indole-7-carbonitrile The product is obtained as for Step A of Example 1 but using the product of Preparation 6 instead of the product of Preparation 3.

Step B

1-{7-[(Dimethylamino)methyl]-2,3,6,7-tetrahydro-1H-cyclobuta[e]indol-7-yl}cyclohexanol The process is as for Example 3, Steps A to D, but using in Step A of that Example the product of Step A above.

EXAMPLE 10

1-[6-(Aminomethyl)-5,6-dihydrocyclobuta[f][1]benzothien-6-yl]cyclohexanol

The product is obtained according to the process of Example 4, Steps A to B, using the compound of Preparation 8 as substrate in Step A.

EXAMPLE 11

1-[6-(Aminomethyl)-5,6-dihydrocyclobuta[f][1]benzofuran-6-yl]cyclohexanol

The product is obtained according to the process of Example 4, Steps A to B, using the compound of Preparation 10 as substrate in Step A.

EXAMPLE 12

1-{6-[(Dimethylamino)methyl]-5,6-dihydrocyclobuta[f][1]benzofuran-6-yl}cyclohexanol The product is obtained according to the process of Example 5, using the compound of Example 11 as substrate.

EXAMPLE 13

1-[6-(Aminomethyl)-6,7-dihydrocyclobuta[e][1]benzothien-6-yl]cyclohexanol

The product is obtained according to the process of Example 4, Steps A to B, using the compound of Preparation 11 as substrate in Step A.

EXAMPLE 14

1-[7-(Aminomethyl)-6,7-dihydrocyclobuta[e][1]benzothien-7-yl]cyclohexanol

The product is obtained according to the process of Example 4, Steps A to B, using the compound of Preparation 12 as substrate in Step A.

EXAMPLE 15

1-[6-(Aminomethyl)-6,7-dihydrocyclobuta[e][1]benzofuran-6-yl]cyclohexanol

The product is obtained according to the process of Example 4, Steps A to B, using the compound of Preparation 13 as substrate in Step A.

EXAMPLE 16

1-[7-(Aminomethyl)-6,7-dihydrocyclobuta[e][1]benzofuran-7-yl]cyclohexanol

The product is obtained according to the process of Example 4, Steps A to B, using the compound of Preparation 14 as substrate in Step A.

EXAMPLE 17

1-{6-[(Dimethylamino)methyl]-5,6-dihydrocyclobuta[f][1]benzothien-6-yl}cyclohexanol The product is obtained according to the process of Example 2, using the compound of Example 10 as substrate.

Melting point: 161–166° C. (M.K.)

EXAMPLE 18

1-{5-[(Dimethylamino)methyl]-5,6-dihydrocyclobuta[f][1,3]benzodioxol-5-yl}cyclohexanol The product is obtained according to the process of Example 1, Steps A to B, and according to the process of Example 2, using the product of Preparation 15 as substrate in Step A of Example 1 instead of the product of Preparation 3.

Melting point: 94–96° C. (M.K.)

EXAMPLE 19

1-{5-[(Dimethylamino)methyl]-5,6-dihydrocyclobuta[f][1]benzofuran-5-yl}cyclopentanol and Its Hydrochloride The product is obtained according to the process of Example 4, Steps A to B, and then according to the process of Example 5, using cyclopentanone as substrate in Step A instead of cyclohexanone. The free base is converted to its hydrochloride by the action of ethereal hydrogen chloride.

Melting point: 258–262° C. (M.K.)

EXAMPLE 20

1-{5-[(Dimethylamino)methyl]-5,6-dihydrocyclobuta[f][1,3]benzodioxol-5-yl}cyclopentanol The product is obtained according to the process of Example 4, Steps A to B, and then according to the process of Example 5, using cyclopentanone as substrate in Step A instead of cyclohexanone and using the product of Preparation 15 instead of the product of Preparation 9.

Melting point: 71–74° C. (M.K.)

EXAMPLE 21

1-[5-(Aminomethyl)-5,6-dihydrocyclobuta[f][1]benzothien-5-yl]cyclopentanol

The product is obtained according to the process of Example 4, Steps A to B, using cyclopentanone as substrate in Step A instead of cyclohexanone and using the product of Preparation 7 instead of the product of Preparation 9.

Melting point: 149–153° C. (M.K.)

EXAMPLE 22

1-{5-[(Methylamino)methyl]-5,6-dihydrocyclobuta[f][1]benzothien-5-yl}cyclopentanol A solution of 0.29 ml of ethyl chloroformate in 40 ml of dichloromethane is introduced, at 0° C., to a mixture of 1 g of the product of Example 21, 1.2 ml of triethylamine and 60 ml of dichloromethane. After returning to room temperature, the reaction mixture is washed with 0.1N hydrochloric acid and then with a saturated sodium hydrogen carbonate solution, dried and then evaporated. The resulting residue is dissolved in 20 ml of tetrahydrofuran. The solution is added to a mixture of 1.3 g of AlLiH$_4$ in 60 ml of tetrahydrofuran. The reaction mixture is refluxed for 3 hours and then hydrolysed with 0.65 ml of water, 0.45 ml of 20% sodium hydroxide solution and 2.1 ml of water. After filtration and concentration, the residue is purified by chromatography over silica gel (dichloromethane/ethanol/NH$_4$OH: 95/5/0.5) and recrystallised from isopropyl ether to yield the expected product.

Melting point: 166–169° C. (M.K.)

EXAMPLE 23

1-{5-[(Dimethylamino)methyl]-5,6-dihydrocyclobuta[f][1]benzothien-5-yl}cyclopentanol The product is obtained according to the process of Example 5, using the product of Example 21 instead of the product of Example 4.

Melting point: 93–98° C. (M.K.)

EXAMPLE 24

(+)-1-{5-[(Dimethylamino)methyl]-5,6-dihydrocyclobuta[f][1]benzothien-5-yl}cyclopentanol The product of Example 23 is injected onto a chiral column with a mobile phase comprising methanol/diethylamine: 1000/1. The first product eluted corresponds to the (+) isomer.

Melting point: 122–126° C. (M.K.)

EXAMPLE 25

(−)-1-{5-[(Dimethylamino)methyl]-5,6-dihydrocyclobuta[f][1]benzothien-5-yl}cyclopentanol The product of Example 23 is injected onto a chiral column with a mobile phase comprising methanol/diethylamine: 1000/1. The second product eluted corresponds to the (−) isomer.

Melting point: 123–127° C. (M.K.)

EXAMPLE 26

1-[6-(Aminomethyl)-5,6-dihydrocyclobuta[f][1]benzothien-6-yl]cyclopentanol

The product is obtained according to the process of Example 4, Steps A to B, using cyclopentanone as substrate in Step A instead of cyclohexanone and using the product of Preparation 8 instead of the product of Preparation 9.

Melting point: 141–143° C. (M.K.)

EXAMPLE 27

1-{6-[(Methylamino)methyl]-5,6-dihydrocyclobuta[f][1]benzothien-6-yl}cyclopentanol The product is obtained according to the process of Example 22, using the product of Example 26 instead of the product of Example 21.

Melting point: 117–120° C. (M.K.)

EXAMPLE 28

1-{6-[(Dimethylamino)methyl]-5,6-dihydrocyclobuta[f][1]benzothien-6-yl}cyclopentanol The product is obtained according to the process of Example 5, using the product of Example 26 instead of the product of Example 4.

Melting point: 94–96° C. (M.K.)

EXAMPLE 29

1-{6-[(Dimethylamino)methyl]-1-methyl-5,6-dihydro-1H-cyclobuta[f]indol-6-yl}cyclopentanol The product is obtained according to the processes of Examples 1, 2 and 8 in succession, and using cyclopentanone in Step A of Example 1 instead of cyclohexanone.

Melting point: 108–111° C. (M.K.)

EXAMPLE 30

1-{5-[(Dimethylamino)methyl]-1-methyl-5,6-dihydro-1H-cyclobuta[f]indol-5-yl}cyclopentanol The product is obtained according to the processes of Examples 1, 2 and 8 in succession, and using cyclopentanone in Step A of Example 1 instead of cyclohexanone and using the product of Preparation 21 instead of the product of Preparation 3.

Melting point: 100–104° C. (M.K.)

EXAMPLE 31

1-{7-[(Dimethylamino)methyl]-6,7-dihydrocyclobuta[g][1]benzofuran-7-yl}cyclopentanol The product is obtained according to the process of Example 4, Steps A to B, and then according to the process of Example 5, using cyclopentanone as substrate in Step A instead of cyclohexanone and using the product of Preparation 16 instead of the product of Preparation 9.

Melting point: 135–137° C. (M.K.)

EXAMPLE 32

1-{6-[(Dimethylamino)methyl]-5,6-dihydrocyclobuta[f][1]benzofuran-6-yl}cyclopentanol and Its Hydrochloride The product is obtained according to the process of Example 4, Steps A to B, and then according to the process of Example 5, using cyclopentanone as substrate in Step A instead of cyclohexanone and using the product of Preparation 10 instead of the product of Preparation 9. The hydrochloride is prepared by the action of ethereal hydrogen chloride.

Melting point (hydrochloride): 225–235° C. (M.K.)

EXAMPLE 33

1-{6-[(Dimethylamino)methyl]-2,3,5,6-tetrahydro-1H-cyclobuta[f]indol-6-yl}cyclopentanol The product is obtained according to the process of Example 3, Steps A to B, in Step A using the product prepared in Step A of Example 1 starting from cyclopentanone and not from cyclohexanone.

Melting point: 105–108° C. (M.K.)

EXAMPLE 34

1-{6-[(Dimethylamino)methyl]-5,6-dihydro-1H-cyclobuta[f]indol-6-yl}cyclopentanol The product is obtained according to the process of Example 8, using the product of Example 33 as substrate.

Melting point: 180–184° C. (M.K.)

EXAMPLE 35

1-{1-[(Dimethylamino)methyl]-1,2-dihydrocyclobuta[b]naphthalen-1-yl}cyclopentanol The product is obtained according to the process of Example 4, Steps A to B, and then according to the process of Example 5, using cyclopentanone as substrate in Step A instead of cyclohexanone and using the product of Preparation 17 instead of the product of Preparation 9.

Melting point: 133–135° C. (M.K.)

EXAMPLE 36

1-{7-[(Dimethylamino)methyl]-6,7-dihydro-3H-cyclobuta[e]indol-7-yl}cyclopentanol The product is obtained according to the process of Example 3, Steps A to D, and then Example 8, in Step A of Example 3 using the product prepared in Step A of Example 1 but on the one hand using the product of Preparation 9 and on the other hand using cyclopentanone.

Melting point: 200–204° C. (M.K.)

EXAMPLE 37

1-{1-[(Dimethylamino)methyl]-1,2-dihydrocyclobuta[a]naphthalen-1-yl}cyclopentanol and Its Hydrochloride The product is obtained according to the process of Example 4, Steps A to B, and then according to the process of Example 5, using cyclopentanone as substrate in Step A instead of cyclohexanone and using the product of Preparation 18 instead of the product of Preparation 9. The hydrochloride is obtained from the ethereal hydrogen chloride.

Melting point (hydrochloride): 258–262° C. (M.K.)

EXAMPLE 38

1-(7-{[(((2S)-2,3-Dihydro-1,4-benzodioxin-2-ylmethyl)amino]methyl}-6,7-dihydrocyclo-buta[g][1]benzofuran-7-yl)cyclopentanol and Its Hydrochloride Step A 1-[7-(Aminomethyl)-6,7-dihydrocyclobuta[g][1]benzofuran-7-yl]cyclopentanol The product is obtained according to the process of Example 4, Steps A to B, using cyclopentanone as substrate in Step A instead of cyclohexanone and using the product of Preparation 16 instead of the product of Preparation 9.

Step B (2R)-N-{[7-(1-Hydroxycyclopentyl)-6,7-dihydrocyclobuta[g][1]benzofuran-7-yl]methyl}-2,3-dihydro-1,4-benzodioxine-2-carboxamide A solution of 762 mg of (2R)-2,3-dihydrobenzo[1,4]dioxin-2-ylcarboxylic acid chloride is added, at 0° C., to 900 mg of the compound obtained in Step A in 30 ml of dichloromethane and 1.2 ml of diisopropylethylamine. After 48 hours at room temperature, the reaction mixture is diluted with water and extracted with dichloromethane. Conventional treatment of the organic phases enables, after evaporation under reduced pressure, the expected product to be isolated in the form of a meringue.

Step C 1-(7-{[(((2S)-2,3-Dihydro-1,4-benzodioxin-2-ylmethyl)amino]methyl}-6,7-dihydrocyclobuta[g][1]benzofuran-7-yl)cyclopentanol and Its Hydrochloride 500 mg of lithium aluminium hydride in 20 ml of tetrahydrofuran are refluxed, and then 1.1 g of the product obtained in Step B dissolved in 20 ml of tetrahydrofuran are added. After 3 hours 30 minutes' reflux, the reaction mixture is hydrolysed by the addition of 0.45 ml of water, 0.31 ml of 20% sodium hydroxide solution and 1.67 ml of water. After filtration and evaporation, chromatography over silica gel (dichloromethane/ethanol: 98/2) enables the expected product to be isolated, which is converted to its hydrochloride by the action of ethereal hydrogen chloride.

Melting point (hydrochloride): 213–235° C.

EXAMPLE 39

1-(5-{[(((2R)-2,3-Dihydro-1,4-benzodioxin-2-ylmethyl)amino]methyl}-5,6-dihydrocyclobuta[f][1,3]benzodioxol-5-yl)cyclopentanol and Its Hydrochloride The product is obtained according to the process of Example 38, Steps A to C, in Step A using the product of Preparation 15 and in Step B using (2S)-2,3-dihydrobenzo[1,4]dioxin-2-ylcarboxylic acid chloride.

Melting point (hydrochloride): 109–119° C. (M.K.)

EXAMPLE 40

1-(1-{[[2-(5-Fluoro-1H-indol-3-yl)ethyl](methyl)amino]methyl}-1,2-dihydrocyclobuta[b]naphthalen-1-yl)cyclopentanol Step A 1-{[(Methyl)amino]methyl}-1,2-dihydrocyclobuta[b]naphthalen-1-yl)cyclopentanol The product is obtained according to the process of Example 22, using 1-[1-(aminomethyl)-1,2-dihydrocyclobuta[b]naphthalen-1-yl]cyclopentanol as substrate, which is obtained starting from Preparation 17.

Step B 2-(5-Fluoro-1H-indol-3-yl)-N-[[1-(1-hydroxycyclopentyl)-1,2-dihydrocyclobuta[b]naphthalen-1-yl]methyl]-N-methylacetamide 0.652 g of (5-fluoro-indol-3-yl)acetic acid dissolved in 30 ml of dichloromethane are treated with 0.61 g of carbonyldiimidazole, at room temperature for 30 minutes. A solution of 0.95 g of the product obtained in Step A dissolved in 5 ml of dichloromethane is poured into the solution. When the reaction is complete, the reaction mixture is taken up in water, decanted, dried and evaporated to yield the expected product.

Step C 1-(1-{[[2-(5-Fluoro-1H-indol-3-yl)ethyl](methyl)amino]methyl}-1,2-dihydrocyclobuta[b]naphthalen-1-yl)cyclopentanol The product is obtained according to the process of Example 39, using the product obtained in the preceding Step B as substrate.

PHARMACOLOGICAL STUDY OF THE COMPOUNDS OF THE INVENTION

A. In Vitro Studies

EXAMPLE 41

Determination of the Affinity for Serotonin Reuptake Sites

The affinity was determined by competition experiments using [$^3$H]-paroxetine (NEN, Les Ulis, France). The membranes are prepared from rat frontal cortex and are incubated in triplicate for 2 hours at 25° C. with 1.0 nM [$^3$H]-paroxetine and cold ligand in a final volume of 0.4 ml. The incubation buffer contains 50 nM TRIS-HCl (pH 7.4), 120 mM NaCl and 5 mM KCl. Non-specific binding is determined using 10 μM citalopram. At the end of the incubation, the incubation medium is filtered and washed three times with 5 ml of cooled buffer. The radioactivity retained on the filters is determined by liquid scintillation counting. The binding isotherms are analysed by non-linear regression to determine the IC$_{50}$ values. Those values are converted into a dissociation constant (K$_i$) using the Cheng-Prusoff equation:

$$K_i = IC_{50}/(1+L/K_d)$$

wherein L is the concentration of [$^3$H]-paroxetine and K$_d$ is the dissociation constant of [$^3$H]-paroxetine for the serotonin reuptake site (0.13 nM). The results are expressed in pK$_i$ (−log K$_i$).

The compounds of the present invention demonstrate very good affinity for serotonin reuptake sites, their pK$_i$ being ≧7.

EXAMPLE 42

Determination of the Affinity for Noradrenalin Reuptake Sites

The affinity was determined by competition experiments using [$^3$H]-nisoxetine (Amersham, les Ulis, France). The membranes are prepared from rat frontal cortex and are incubated in triplicate for 4 hours at 4° C. with 2 nM [$^3$H]-nisoxetine and cold ligand in a final volume of 0.5 ml. The incubation buffer contains 50 mM TRIS-HCl (pH 7.4), 300 mM NaCl and 5 mM KCl. Non-specific binding is determined using 10 μM desipramine. At the end of the incubation, the incubation medium is filtered and washed three times with 5 ml of cooled filtration buffer (50 mM TRIS-HCl, pH 7.4, 300 mM NaCl and 5 mM KCl). The radioactivity retained on the filters is determined by liquid scintillation counting. The binding isotherms are analysed by non-linear regression to determine the IC$_{50}$ values. Those values are converted into a dissociation constant (K$_i$) using the Cheng-Prusoff equation:

$$K_i = IC_{50}/(1+L/K_d)$$

wherein L is the concentration of [$^3$H]-nisoxetine and K$_d$ is the dissociation constant of [$^3$H]-nisoxetine for the noradrenalin reuptake site (1.23 nM). The results are expressed in pKi (−log Ki).

The pKi of the compounds of the invention is ≧6.

B. In Vivo Studies

EXAMPLE 43

Microdialysis Experiment in the Rat

Rats are anaesthetised with pentobarbital (60 mg/kg i.p.). They are placed in a Kopf stereotactic device and the cannula guide is implanted in the cingulate frontal cortex in accordance with the coordinates described in the Paxinos and Watson atlas (1982) as follows: AP=+2.2; L=±0.6; DV=−0.2. The rats are placed in separate cages and are not used in dialysis until 5 days later. On the day of the dialysis, the probe is slowly lowered and held in position. The probe is perfused at a flow rate of 1 μl/mn with a solution of 147.2 mM NaCl, 4 mM KCl and 2.3 mM CaCl$_2$ adjusted to pH 7.3 with a phosphate buffer (0.1 M). Two hours after implantation, samples are collected every 20 minutes for 4 hours. Three baseline samples are taken before administration of the products to be tested. The rats are left in their individual cages for the whole of the experiment. When the experiment is finished, the rats are decapitated and the brain is removed and frozen in isopentane. Sections of a thickness of 100 μm are cut and stained with cresyl violet, which allows verification of the location of the probes.

The simultaneous quantification of dopamine, norepinephrine and serotonin is carried out as follows: 20 μl dialysis samples are each diluted with 20 μl of mobile phase (NaH$_2$PO$_4$: 75 mM, EDTA: 20 μM, sodium 1-decanesulphonate: 1 mM, methanol: 17.5%, triethylamine: 0.01%, pH: 5.70) and 33 μl samples are analysed by HPLC using a reverse phase column thermostatically maintained at 45° C. and quantified by means of a coulometric detector. The potential of the first electrode of the detector is set at −90 mV (reduction) and that of the second at +280 mV (oxidation). The mobile phase is injected at a flow rate of 2 ml/mn using a pump. The sensitivity limits for dopamine, norepinephrine and serotonin are 0.55 fmol per sample. All the products of the invention are injected subcutaneously in a volume of 1.0 ml/kg. The products are dissolved in distilled water to which a few drops of lactic acid have been added if necessary.

Results

By way of example and in order to illustrate the activity of the products of the invention, the compound of Example 5, administered subcutaneously at a dose of 10 mg/kg, increases the level of serotonin by: 250±15%, that of noradrenalin by 500±13% and that of dopamine by 400±50% (maximum % of the effect compared with the baseline level defined as 0%).

EXAMPLE 44

Marble-Burying Test in Mice

This test enables evaluation of the capacity of pharmacological agents to inhibit the spontaneous marble-burying behaviour of mice, the inhibition being predictive of anti-depressant and/or anti-impulsive action. Male mice of the NMRI strain (Iffa-Credo, l'Arbresle, France) weighing from 20 to 25 g on the day of the experiment are placed individually in Macrolon® boxes (30×18×19 cm) containing 5 cm of sawdust and covered with a perforated plexiglass plate. Twenty-four "tiger's eye" glass marbles are evenly distributed on the sawdust at the periphery of the box. At the end of 30 minutes' free exploration, the animals are removed from the box and the number of buried marbles is counted.

Results

By way of example, the Table shows the effect of a product of the invention compared with the effect of fluoxetine, a reference antidepressant.

| Example | Marble-burying in mice, ID$_{50}$ |
|---------|------------------------------------|
| Fluoxetine | 8.03 |
| 5 | 0.6 |

ID$_{50}$ =inhibitory dose$_{50}$
The doses are expressed in mg/kg s.c.

EXAMPLE 45

Pharmaceutical Composition: Tablets

Formulation for the preparation of 1000 tablets containing a dose of 5 mg

Compound of Example 5
5 g
Hydroxypropylmethylcellulose
5 g
Wheat starch
10 g
Lactose
100 g
Magnesium stearate
2 g

What is claimed is:

1. A compound selected from those of formula (I):

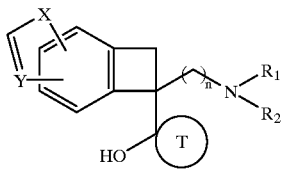

(I)

wherein:

----- denotes single bond or double bond, n is integer from 1 to 6 inclusive, $R_1$ and $R_2$, which may be, identical or different, each independently of the other, represent a group selected from hydrogen, linear or branched ($C_1$–$C_6$)alkyl, aryl, aryl-($C_1$–$C_6$)alkyl in which alkyl is linear or branched, cycloalkyl, cycloalkyl-($C_1$–$C_6$)alkyl in which alkyl is linear or branched, linear or branched ($C_2$–$C_6$)alkenyl, linear or branched ($C_2$–$C_6$)alkynyl, heterocycloalkyl, heterocycloalkyl-($C_1$–$C_6$)alkyl in which alkyl is linear or branched, heteroaryl, and heteroaryl-($C_1$–$C_6$)alkyl in which alkyl is linear or branched, X represents a group selected from —CH=CH—, oxygen, S(O)$_m$ wherein m is integer from 0 to 2 inclusive, and NR$_3$ wherein R$_3$ represents a group selected from hydrogen, linear or branched ($C_1$–$C_6$) alkyl, aryl, aryl-($C_1$–$C_6$)-alkyl in which alkyl is linear or branched, cycloalkyl, cycloalkyl-($C_1$–$C_6$)alkyl in which alkyl is linear or branched, linear or branched ($C_2$–$C_6$)alkenyl, and linear or branched ($C_2$–$C_6$) alkynyl, Y represents CH or CH$_2$ depending on whether

----- denotes single bond, or double bond, or may have the additional meaning of oxygen when X represents oxygen, T represents monocyclic or polycyclic ($C_3$–$C_{12}$) cycloalkyl, wherein one of carbon of cycloalkyl may optionally be replaced by a group selected from oxygen, selenium, S(O)$_p$ wherein p is integer from 0 to 2 inclusive, NR$_3$ wherein R$_3$ is as defined hereinbefore, and SiR$_4$R$_5$ wherein R$_4$ and R$_5$, which may be identical or different, represent linear or branched ($C_1$–$C_6$)alkyl, its isomers and addition salts thereof with a pharmaceutically acceptable acid or base, it being understood that:
  "aryl" is understood to mean a group selected from phenyl, biphenyl, naphthyl, dihydronaphthyl, tetrahydronaphthyl, indanyl, indenyl and benzocyclobutyl, it being possible for each of those groups to be optionally substituted by one or more, identical or different, groups selected from halogen, linear or branched ($C_1$–$C_6$)alkyl, hydroxy, linear or branched ($C_1$–$C_6$)alkoxy, nitro, cyano, linear or branched trihalo-($C_1$–$C_6$)alkyl, amino, monoalkylamino in which alkyl has from 1 to 6 carbon atoms and is linear or branched, and dialkylamino in which each alkyl has from 1 to 6 carbon and is linear or branched,
  "heteroaryl" is understood to mean aryl as defined hereinbefore, containing within the ring system from one to three, identical or different, hetero atoms selected from oxygen, nitrogen and sulphur, said heteroaryl being optionally substituted by one or more, identical or different, groups selected from substituents defined above for aryl,
  "cycloalkyl" is understood to mean mono- or polycyclic system, having from 3 to 12 ring members, optionally containing one or more unsaturations, which do not confer aromatic character upon the said ring system,
  "heterocycloalkyl" is understood to mean cycloalkyl as defined hereinbefore, containing within the ring system from one to three, identical or different, hetero atoms selected from oxygen, nitrogen, and sulphur.

2. A compound of claim 1, wherein n has the value 1.

3. A compound of claim 1, wherein $R_1$ and $R_2$, which may be, identical or different, represent hydrogen, linear or branched ($C_1$–$C_6$)alkyl, or 2,3-diydro-1,4-benzodioxin-2-ylmethyl.

4. A compound of claim 1, wherein T represnts saturated monocyclic ($C_3$–$C_8$)cycloalkyl.

5. A compound of claim 1, wherein T represents cyclopentyl, or cyclohexyl.

6. A compound of claim 1, wherein is it a compound of formula (I/A):

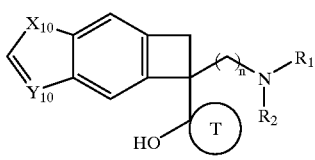

(I/A)

wherein n, $R_1$, $R_2$, and T are as defined for formula (I), $X_{10}$ represents oxygen or sulphur, and $Y_{10}$ represents CH.

7. A compound of claim 1, wherein it is a compound of formula (I/B):

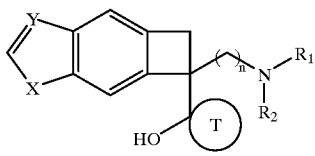

(I/B)

wherein X, Y, n, $R_1$, $R_2$, $R_3$, and T are as defined for formula (I).

8. A compound of claim 7, wherein n is 1, and X represents $NR_3$ wherein $R_3$ represents hydrogen or linear or branched $(C_1-C_6)$alkyl.

9. A compound of claim 1, wherein it is a compound of formula (I/C):

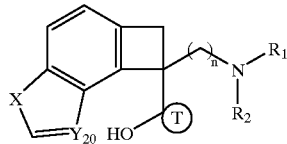

(I/C)

wherein n, $R_1$, $R_2$, X, and T are as defined for formula (I), and $Y_{20}$ represents CH or $CH_2$.

10. A compound of claim 1, wherein it is a compound of formula (I/D):

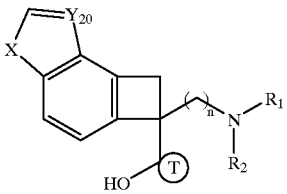

(I/D)

wherein n, $R_1$, $R_2$, X, and T are as defined for formula (I), and $Y_{20}$ represents CH or $CH_2$.

11. A compound of claim 1, wherein it is a compound of formula (I/E):

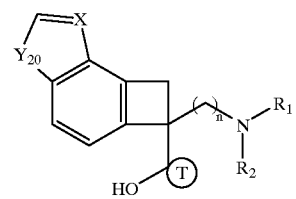

(I/E)

wherein n, $R_1$, $R_2$, X, and T are as defined for formula (I), and $Y_{20}$ represents CH or $CH_2$.

12. A compound one of claim 1, wherein it is a compound of formula (I/F):

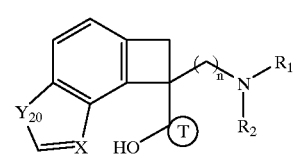

(I/F)

wherein n, $R_1$, $R_2$, X, and Y are as defined for formula (I), and $Y_{20}$ represents CH or $CH_2$.

13. A compound of claim 1 selected from
- 1-{6-[(dimethylamino)methyl]-1-methyl-2,3,5,6-tetrahydro-1H-cyclobuta[ff]indol-6- yl}cyclohexanol,
- 1-{6-[(dimethylamino)methyl]-2,3,5,6-tetrahydro-1H-cyclobuta[f]indol-6-yl}cyclohexanol,
- 1-{5-[(dimethylamino)methyl]-5,6-dihydrocyclobuta[f][1]benzofuran-5-yl}cyclohexanol,
- 1-{5-[(dimethylamino)methyl]-5,6-dihydrocyclobuta[f][1]benzothien-5-yl}cyclohexanol,
- 1-{6-[(dimethylamino)methyl]-1-methyl-5,6-dihydro-1H-cyclobuta[f]indol-6-yl}cyclohexanol,
- 1-{7-[(dimethylamino)methyl]-2,3,6,7-tetrahydro-1H-cyclobuta[e]indol-7-yl}cyclohexanol,
- 1-{5-[(emthylamino)methyl]-5,6-dihydrocyclobuta[f][1]benzothien-5-yl}cyclopentanol,
- 1-{5-[(dimethylamino)methyl]-5,6-dihydrocyclobutal[f][1]benzothien-5-yl}cyclopentanol,
- (+)-1-{5-[(dimethylamino)methyl]-5,6-dihydrocyclobuta[f][1]benzothien-5-yl}cyclopentanol,
- (−)-1-{5-[(dimethylamino)methyl]-5,6-dihydrocyclobuta[f][1]benzothien-5-yl}cyclopenthanol,
- 1-{6-[(dimethylamino)methyl]-5,6-dihydrocyclobuta[f][1]benzothien-6-yl}cyclopentanol,
- 1-{5-[(dimethylamino)methyl]-1-methyl-5,6-dihydro-1H-cyclobutal[f]indol-5-yl}cyclopentanol,
- 1-{7-[(dimethylamino)methyl]-6,7-dihydrocyclobuta[g][1]benzofuran-7-yl}cyclopentanol,
- 1-{1-[(dimethylamino)methyl]-1,2-dihydrocyclobutal[b]naphthalen-1-yl}cyclopentanol,
- 1-{7-[(dimethylamino)methyl]-6,7-dihydro-3H-cyclobuta[e]indol-7-yl}cyclopentanol, and
- 1-{1-[(dimethylamino)methyl]-1,2-dihydrocyclobutal[a]naphthalen-1yl}cyclopentanol.

its isomers and addition salts thereof with a pharmaceutically-acceptable acid or base.

14. A method for treating a living animal body afflicted with a disease selected from depression, panic attacks, obsessive-compulsive disorders, phobias, impulsive disorders, drug abuse, anxiety, obesity, and boulimia, comprising the step of administering to the living body an amount of a compound of claim 1 which is effective for alleviation of said disease.

15. A pharmaceutical composition useful in treating depression, panic attacks, obsessive-compulsive disorders, phobias, impulsive disorders, drug abuse, anxiety, obesity, and boulimia, comprising as active principle an effective amount of a compound of claim 1, in combination with one or more pharmaceutically-acceptable excipients or vehicles.

* * * * *

UNITED STATES PATENT AND TRADEMARK OFFICE
CERTIFICATE OF CORRECTION

PATENT NO. : 6,420,413 B2
DATED : July 16, 2002
INVENTOR(S) : Jean-Louis Peglion et al.

It is certified that error appears in the above-identified patent and that said Letters Patent is hereby corrected as shown below:

<u>Title page,</u>
Item [73], Assignee, "Laboratories" should read -- Laboratoires --.
Item [57], ABSTRACT,
Second to last line, please add a comma after the word "same" and remove the word "are".

<u>Column 35,</u>
Line 47, "$CH_2$'" should read -- $CH_2$ --.

Formula (I/D): 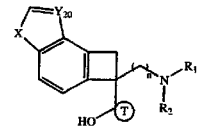 should be 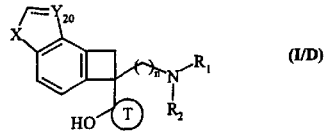

<u>Column 36,</u>
Formula (I/E): 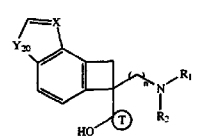 should be 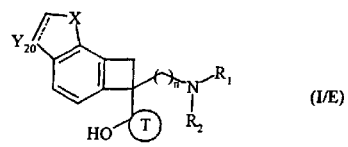

Formula (I/F): 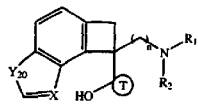 should be 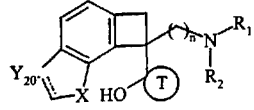

Lines 29-53, "[F]" should read -- [*f*] --.
Line 40, "[e]" should read -- [*e*] --.
Line 41, "emthylamino" should read -- methylamino --.

UNITED STATES PATENT AND TRADEMARK OFFICE
CERTIFICATE OF CORRECTION

PATENT NO.    : 6,420,413 B2
DATED         : July 16, 2002
INVENTOR(S)   : Jean-Louis Peglion et al.

It is certified that error appears in the above-identified patent and that said Letters Patent is hereby corrected as shown below:

<u>Column 36 (cont'd),</u>
Line 54, "[g]" should read -- [$g$] --.
Line 57, "[b]" should read -- [$b$] --.
Line 60, "[e]" should read -- [$e$] --.
Line 61, "[a]" should read -- [$a$] --.

Signed and Sealed this

Twelfth Day of November, 2002

Attest:

JAMES E. ROGAN
Attesting Officer                Director of the United States Patent and Trademark Office